US008673056B2

(12) United States Patent
De Bas et al.

(10) Patent No.: US 8,673,056 B2
(45) Date of Patent: Mar. 18, 2014

(54) PROCESS AND APPARATUS FOR THE PURIFICATION OF METHANE RICH GAS STREAMS

(75) Inventors: Mathieu André De Bas, Gouda (NL); Jacob Kuiper, Den Haag (NL); Jeroen De Pater, Oud-Vossemeer (NL)

(73) Assignee: Gastreatment Services B.V., Bergambacht (NL)

( * ) Notice: Subject to any disclaimer, the term of this patent is extended or adjusted under 35 U.S.C. 154(b) by 0 days.

(21) Appl. No.: 12/063,916

(22) PCT Filed: Aug. 17, 2006

(86) PCT No.: PCT/NL2006/000427
§ 371 (c)(1),
(2), (4) Date: Jul. 28, 2008

(87) PCT Pub. No.: WO2007/021183
PCT Pub. Date: Feb. 22, 2007

(65) Prior Publication Data
US 2008/0282612 A1    Nov. 20, 2008

(30) Foreign Application Priority Data
Aug. 17, 2005   (EP) .................... 05076906

(51) Int. Cl.
*B01D 53/00*    (2006.01)
(52) U.S. Cl.
USPC ........ 95/41; 95/114; 95/139; 62/613; 62/619; 62/401; 96/128; 96/142
(58) Field of Classification Search
USPC .......................................... 95/236
See application file for complete search history.

(56) References Cited

U.S. PATENT DOCUMENTS

| 3,312,073 | A | * | 4/1967 | Harmens et al. ............... 62/613 |
| 3,358,461 | A | * | 12/1967 | Hendrix ......................... 62/635 |
| 3,372,555 | A | * | 3/1968 | Becker ........................... 62/632 |
| 4,566,278 | A | * | 1/1986 | Force ............................. 60/618 |
| 4,681,612 | A | * | 7/1987 | O'Brien et al. ................. 62/624 |
| 4,704,146 | A | * | 11/1987 | Markbreiter et al. .......... 62/625 |

(Continued)

FOREIGN PATENT DOCUMENTS

| BE | 759065 | 5/1971 |
| CH | 692653 A5 | 9/2002 |

(Continued)

*Primary Examiner* — Duane Smith
*Assistant Examiner* — Pankti Patel
(74) *Attorney, Agent, or Firm* — Hoffmann & Baron, LLP

(57) ABSTRACT

The invention is directed to processes and apparatuses for gas treatment, in particular for the purification of methane rich gas streams, such as gas obtained from the conversion from organic matter ("biogas"). In accordance with the present invention there is provided an apparatus and a process for producing a purified methane comprising gas stream (P) from a methane containing gas stream (A), comprising the steps of: (a) pressurising said methane containing gas stream (A) and subsequently cooling it, whereby a stream comprising condensed contaminants (C) and a methane comprising stream (B) are obtained; (b) optionally feeding said methane comprising stream (B) to an adsorption unit and/or a catalytic conversion unit, whereby the concentration of contaminants in stream (B) is further decreased; and (c) cooling the methane comprising stream (B) to a temperature which is sufficient to condensate $CO_2$ from said stream (B), whereby said purified methane comprising gas stream (P) is obtained.

17 Claims, 4 Drawing Sheets

Diagram GPP

(56) References Cited

U.S. PATENT DOCUMENTS

Figure 1:
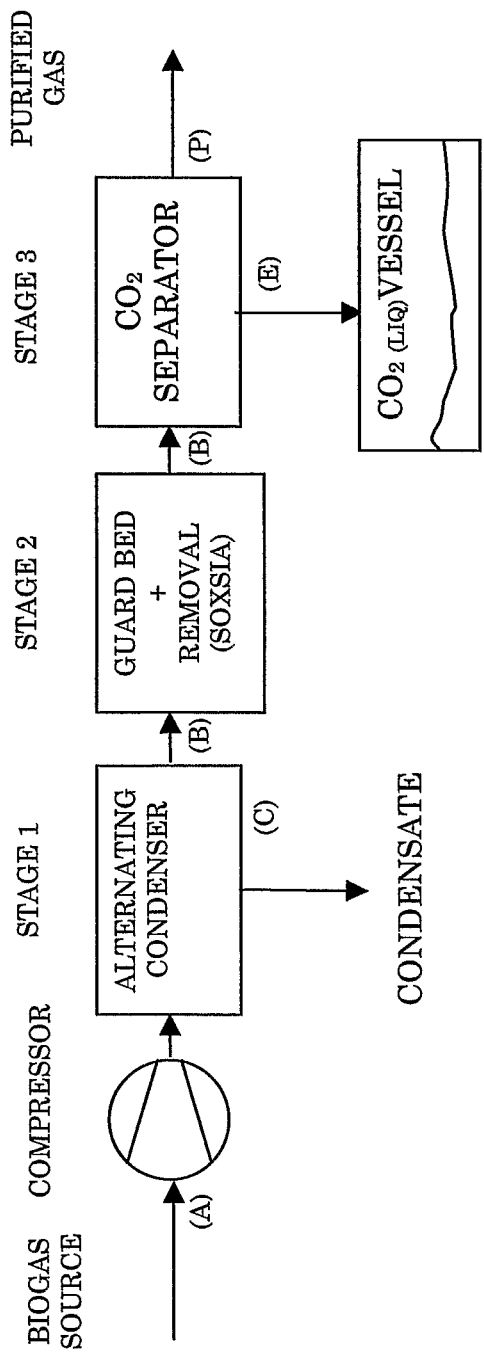

| | | | |
|---|---|---|---|
| 4,770,676 A * | 9/1988 | Sircar et al. | 95/99 |
| 5,615,561 A * | 4/1997 | Houshmand et al. | 62/611 |
| 5,642,630 A * | 7/1997 | Abdelmalek et al. | 62/632 |
| 5,681,360 A * | 10/1997 | Siwajek et al. | 48/127.3 |
| 6,053,007 A * | 4/2000 | Victory et al. | 62/619 |
| 6,257,018 B1 * | 7/2001 | Kelly et al. | 62/617 |
| 7,000,427 B2 * | 2/2006 | Mathias et al. | 62/612 |
| 2003/0047521 A1 * | 3/2003 | McGinness | 210/758 |
| 2004/0045440 A1 * | 3/2004 | Baseen et al. | 95/288 |
| 2006/0248921 A1 * | 11/2006 | Hosford et al. | 62/611 |

FOREIGN PATENT DOCUMENTS

| | | |
|---|---|---|
| EP | 0596 470 A1 | 5/1994 |
| GB | 1170022 | 11/1969 |
| GB | 1565615 | 4/1980 |
| WO | 2004/045745 A1 | 6/2004 |

\* cited by examiner

Stage 3 GPP

PROCESS AND APPARATUS FOR THE PURIFICATION OF METHANE RICH GAS STREAMS

This application is the U.S. National Phase of, and Applicant claims priority from, International Application Number PCT/NL2006/000427 filed 17 Aug. 2006 and European Application bearing Serial No. 05076906.6 filed 17 Aug. 2005, which are incorporated herein by reference.

BACKGROUND OF THE INVENTION

The invention is directed to a process and an apparatus for gas treatment, in particular for the purification of methane rich gas streams, such as gas obtained from the conversion of waste or other types of organic matter ("biogas"). More in particular, the present invention is directed to the production of purified biogas (such as landfill gas, digester gas), which finds use as an efficient energy source. Thus, the present invention is directed to a process and an apparatus to purify such methane rich gases to obtain a gas of a quality that is comparable to that of natural gas.

Various methods are known to produce biogas from organic matter, e.g. by the anaerobic digestion of organic waste (including manure, wastewater sludge, municipal solid waste, etc.). Apart from methane, these fermentation processes usually also produce together large quantities of $CO_2$ (typically about 30-50 vol. % of the produced gas volume may be $CO_2$) and smaller quantities of sulphides and compounds such as vinyl chloride as well as other impurities. The gas must be removed with mechanical work and then treated before it can be used as an energy source. The purified gas can be transported in cylinders, liquefied in cryogenic tanks, used for on-site power generation or piped to a nearby energy demand. The last two options appear to have the widest growth potential.

Methane gas is produced in large quantities in for example, landfill sites and certain sewage works. It is currently recovered in a few locations but the bulk of this potentially valuable energy reserve is lost. Exploitation of landfill gas, digester gas and other types of biogas has been limited particularly because no equipment is available for economically processing the gas into transportable form, which includes purification of the gas. Desirably the equipment itself should be transportable since, in many cases (e.g. landfill sites), the gas source will only produce viable quantities of gas for a limited time and the installation of permanent plant would not be justified.

Removing moist, $H_2S$, $SO_2$, halogens, siloxanes and/or other contaminants is essential to purifying landfill gas, digester gas and biogas for use as an efficient energy source. Although several well established technologies are used, the provision of a viable process for cleaning landfill gas, digester gas and biogas remains a problem. Various methods of gas treatment processes are already known for this purpose. These processes are focused on either the reduction of the moisture level content, $CO_2$ extraction, $H_2S$ removal or the removal of one or more contaminants present in the gas mixture. The disadvantage of the known methods is that they do not to a sufficient extent permit the removal of many of the undesirable substances comprised in gases of the above-mentioned kind. Moreover, present processes are not entirely without disadvantages regarding the level of engine corrosion, wear, maintenance costs, generated process waste, disposal costs and composition of gas mixture as end-product. Finally, the prior art does not show how substances that are removed may be reused.

GB-A-1 565 615 describes a process for the separation of $CO_2$ from methane wherein the mixture of the two compounds is cooled two form a gas/liquid mixture which is subsequently fractionated.

U.S. Pat. No. 4,681,612 describes a process for separating a landfill gas to produce a $CO_2$ product stream and a fuel-grade methane product stream. The process involves cryogenic distillation and a membrane separation step to produce the fuel-grade methane stream.

In the art, also contaminants absorption processes, such as processes based on activated carbon filters, in which most contaminants are removed, are known. However, the regeneration costs and disposal costs for activated carbon are high. In addition carbon filters have a great affinity for moisture thus reducing adsorption efficiency. Furthermore, other absorption methods are applied such as molecular membrane filters, activated polymeric membrane filters and silica-gel. Yet, methods used still do not achieve quality level necessary for use as an efficient energy source.

Other absorption methods include contaminants elimination through organic dissolution. This process is in practice rather complicated because the contaminants targeted are highly volatile. Due to its chemical affinity for water or $CO_2$, it is also possible to remove siloxanes by using condensation methods. In general however, lower elimination levels are achieved through this method.

The chemical make up of the landfill gas, digester gas and biogas differs from site to site. Some sites may have higher sulphur content, while others may have higher traces of siloxanes, and still others may have traces of heavy hydrocarbons, which can increase the risk of engine knocking when the gas is applied in a gas engine. As such, the gas treatment system has to be customized for each site depending on the levels of contaminants and engine requirements. Typical requirements for a biogas to be used in a gas engine are given in Table 1.

TABLE 1

Minimum acceptable level of contaminants for gas engines

| Contaminant | Level | Remarks |
|---|---|---|
| Hydrogen Sulphide | <200 mg/Nm³ methane | Engine corrosion |
| Halides (Chlorine, Fluorine) | <100 mg/Nm³ methane | Engine corrosion |
| Ammonia | <50 mg/Nm³ methane | — |
| Particulates (Dust) | <3-10 μm | — |
| Hydrocarbons > C5 | <5 mg/Nm³ methane | Increase engine knocking |
| Siloxanes *) | <2 mg/Nm³ methane | Increase maintenance Reduced engine performance |
| Moisture | <80% RH at lowest temperature | Acid formation |

*) Depending on maintenance interval as contracted with gas engine manufacturer. Indicated value is average.

Of these contaminants siloxanes are the most aggressive and usually pose the biggest problems. Siloxanes break down into a white abrasive powder, which may damage equipment installed downstream (boilers, combustion engines, turbines, catalysts, or the like). Also, traces of siloxanes, hydrogen sulphide, halogens and other minerals have been reducing the performance and increasing maintenance of the generators. To the present inventor's best knowledge, to date no complete package is offered to remove large part of moist, $H_2S$, $SO_2$, halogens, siloxanes and other contaminants involved.

An object of the present invention is to provide a method which will permit the removal of several of the contaminating substances comprised in biogas. A further object is that the removal of those substances may take place in a simple manner so that the method is not dependent on complicated technical installations. Furthermore, the process of the invention should provide a clean gas having a level of contaminants that is sufficiently low to allow for problem-free application in for instance a gas engine. In other words, in accordance with the present invention the end-product should have a composition that provides a product that is close to natural gas quality. A further object is the process of the present invention should produce as little waste as possible and should be energy efficient.

SUMMARY OF THE INVENTION

It was found that these objects can be met by a process wherein a biogas stream is purified by employing at least two cooling steps. Thus, in a first aspect the present invention is directed to a process for producing a purified methane comprising gas stream (P) from a methane containing gas stream (A), comprising the steps of:

(a) pressurising said methane containing gas stream (A) and subsequently cooling it, whereby a stream comprising condensed contaminants (C) and a methane comprising stream (B) are obtained;

(b) optionally feeding said methane comprising stream (B) to an adsorption unit and/or a catalytic conversion unit, whereby the concentration of contaminants in stream (B) is further decreased; and (c) cooling the methane comprising stream (B) to a temperature which is sufficient to condensate $CO_2$ from said stream (B), whereby said purified methane comprising gas stream (P) is obtained and a stream (E) comprising $CO_2$. It is preferred to carry out optional step (b).

In one embodiment the gas treatment process of the present invention may comprise three steps. In the first step biogas (or any other methane containing gas that needs to be purified) is pressurised and fed to an alternating condenser wherein moist (water), $H_2S$, $SO_2$, halogens, siloxanes and other contaminants are removed from the gas mixture. Next, the gas mixture is fed to a so-called polisher device, containing a suitable catalyst/adsorbent to remove remaining contaminant traces.

Suitable catalyst/absorbents are materials that comprises a desulphurization agent, such as iron oxide $Fe_2O_3$. After the desulphurization agent has reacted with the sulphur compound, it may be reactivated, e.g. by reacting it with oxygen (e.g. from air). The catalyst/absorbents preferably also comprises a adsorbing function, e.g. provided by its pores, which enable adsorption of other contaminants like siloxanes in the pores.

One suitable catalyst/adsorbent that has been developed by the present inventors and that will be marketed under the trade name SOXSIA™ and is designed to convert $H_2S$ to elementary sulphur and to adsorb other contaminants like siloxanes in the pores of the SOXSIA™ adsorbent.

When the desulphurization agent in the catalyst/absorbent is for instance iron oxide, $Fe_2O_3$, $H_2S$ may be removed by the chemical reaction: $Fe_2O_3 + 3H_2S \rightarrow Fe_2S_3 + 3H_2O$.

The catalyst/absorbent can by reactivated using oxygen from air by means of the reaction: $2Fe_2S_3 + 3O_2 \rightarrow 2Fe_2O_3 + 6S$.

During reactivation, the elementary sulphur may be retained in the pores of the adsorbent. For reactivation, a small flow of air is circulated though the catalyst bed. Since the reactivation reaction is exothermic, heat is produced. This heat will consequently evaporate the adsorbed siloxanes and other contaminants and the catalyst/absorbent is regained in its regenerated form.

After each reactivation, the performance of the catalyst on desulphurization is reduced due to the retaining sulphur. To regenerate the catalyst and return to 100% performance, the sulphur is preferably removed by heating en melting of the elementary sulphur using an inert gas such as nitrogen at elevated temperature, e.g. at temperatures of 200-300° C.

The regeneration is preferably performed in a separate unit. Therefore, in general the spent catalyst/absorbent will be replaced with fresh one after which the spent catalyst/absorbent can be regenerated, etc.

The process may then be concluded with a deep cooling process to achieve $CO_2$ removal by partial condensation of the $CO_2$ and removal thereof from the gas.

The undesirable compounds (contaminants) of the gas are extracted, and may be reused. The purified gas end-product produced in accordance with the present invention was found to be equivalent to natural gas (sellable gas) quality, typically having a composition that meets the requirements given in Table 1 hereinabove, and can be injected in the natural gas grid. It may also be compressed so it can be used as fuel for vehicles (CNG=Compressed Natural Gas) or used as a fuel for LNG (Liquefied Natural Gas).

DETAILED DESCRIPTION OF THE INVENTION

In a preferred embodiment, the first step comprises chilling the methane containing gas stream (A) using a heat-exchanger. Very suitable is a triple tube gas/gas-heat exchanger, wherein the triple tube is used to collect the ice formation without causing obstruction in the heat exchangers for a certain period of time. In this way a constant gas flow for a prolonged period of time can be provided. Preferably the cooling in step (a) is carried out to a temperature of approximately −25° C. By chilling the gas moisture and most other contaminants condense. It was found that as the moisture freezes, it maytrap the contaminants, thereby reducing the chance for carryover in the outgoing treated gas, which improves process efficiency considerably. Moisture residue is separated and drained at various chilling and separation points. In this way, nearly all (e.g. up to 99 wt. %) of the water in the gas stream may be condensed or frozen out. In this way, it can be attained that most of the heavy hydrocarbons (viz. $C_5$ or higher) can also condense, and virtually all siloxanes can also be removed. So by removing a considerable part of the remaining moisture, the adsorption efficiency of the adsorber and/or catalytic conversion unit in step (b) is drastically improved; and the chance for condensation down stream of the GPP is virtually eliminated.

Optionally in step (b) particulate matter (typically having a size of from 0.3 to 0.6 μm) can be removed, for instance using an adsorption unit and/or a catalytic conversion unit, such as a single unit comprising a bed of solid particles, such as SOXSIA™ mentioned hereinabove.

In accordance with the present invention there may be produced a clean, energy-rich methane gas, having a methane content up to 90 mole %. For comparison Groningen natural gas contains 81.3 mole % CH4 where High-Cal natural gas contains more than 90 mole % CH4.

Typical removal rates of contaminants (expressed as the amount in weight that is removed) are given in Table 2.

TABLE 2

Typical contaminants removal of the present invention

| Contaminant | Typical Removal Rate | Method |
|---|---|---|
| Moisture | >99% | Condense and freeze |
| Siloxanes | >95% | Condense |
| Particulates (Dust) | >98% | Filtration and washing of gas |
| Hydrocarbons > C5 | >80% | Condense |
| Ammonia | Solubility: 89 g/100 cc | Washing (soluble in water) |
| Hydrogen Sulphide | Solubility: 437 g/cc | Washing (soluble in water) |
| Halides (Chlorine, Fluorine) | | Washing (very soluble in water) |

The gas treated in step (a) may subsequently be conducted through a re-polisher in step (b). The re-polisher is preferably either an activated coal absorber or a catalyst conversion unit, for instance using SOXSIA™ mentioned above. Suitable characteristics of activated coal are given in Table 3. By removing a large percentage of the contaminants in step (a) any trace levels of contaminants in the treated gas can be removed by a fraction of the previously required activated carbon.

TABLE 3

General characteristics of activated extruded carbon

| Butane adsorption at | | |
|---|---|---|
| p/po = 0.42 | 22 | g/100 g |
| p/po = 0.1 | 20 | g/100 g |
| p/po = 0.01 | 17 | g/100 g |
| Benzene adsorption at p/po = 0.1 | 32 | g/100 g |
| Total surface area (BET) | 1100 | m²/g |
| Carbon tetrachloride activity | 60 | g/100 g |
| Apparent density | 510 | kg/m3 |
| Ball-pan hardness | 99 | |
| Particle size > 2.36 mm | 99 | mass-% |
| Ash content | 5 | mass-% |
| Moisture (as packed) | 1 | mass-% |
| Ignition temperature, above | 450 | ° C. |

Alternatively, an adsorbent/catalyst, such as SOXSIA™, or the like may be applied. Typically a catalyst with a particle diameter of 3 mm and length of 8 mm is used. The favourable adsorption properties result in high adsorption capacity and removal efficiency for contaminants present at moderate concentrations in gas flows. The extruded particle shape allows a low pressure drop over the filter. The catalyst/absorbent allows for conversion of sulphur compounds, in particular $H_2S$ into elementary sulphur and also for adsorption of other contaminants, such like siloxanes in the pores of the SOXSIA™ adsorbent.

The desulphering agent is preferably iron oxide, $Fe_2O_3$, which allows for removal of $H_2S$ by the chemical reaction: $Fe_2O_3 + 3H_2S \rightarrow Fe_2S_3 + 3_2O$. It may subsequently be reactivated using oxygen, e.g. from air by the reaction: $2Fe_2S_3 + 3O_2 \rightarrow 2Fe_2O_3 + 6S$.

During reactivation, the elementary sulphur may be retained in the pores of the adsorbent. For reactivation, a small flow of oxygen comprising gas, such as air is contacted with the catalyst/adsorbent, e.g. by circulation though the catalyst/adsorbent bed. Since in general the reactivation reaction is exothermal, heat is produced. This heat will consequently evaporated the adsorbed siloxanes and other contaminants.

After reactivation, the performance of the catalyst/adsorbent may be reduced due to the fact that some sulphur may be retained. To remove the sulphur completely or almost completely, the catalyst/adsorbent can be heated to a temperature that is sufficient for elemental sulphur to melt, preferably in an inert gas, such as using nitrogen. Preferred temperatures are above 300° C.

Next, in step (c), the methane comprising stream (B) is cooled to a temperature which is sufficient to condensate $CO_2$ from said stream (B).

Deep-cooling of the gas mixture is typically attained through three steps. By reducing the temperature of the gas mixture down to approximately −60° C. the dew point of $CO_2$ is reached, and condensation of $CO_2$ appears. In these conditions, approximately 50% of the present $CO_2$ can be liquefied.

Using the Wobbe Index of the outlet gas (P) composition, the final temperature of the gas can be be controlled. At this final temperature the vapour/liquid equilibrium may be chosen such that it corresponds to the required Wobbe Index. This final temperature will preferably vary between −65° C. and −80° C., depending on the required gas composition. From FIG. 3, "Isotherms of $CH_4/CO_2$ binary", it follows that the final temperature will decrease as the final mole fraction of $CH_4$ increases.

Figure 4:
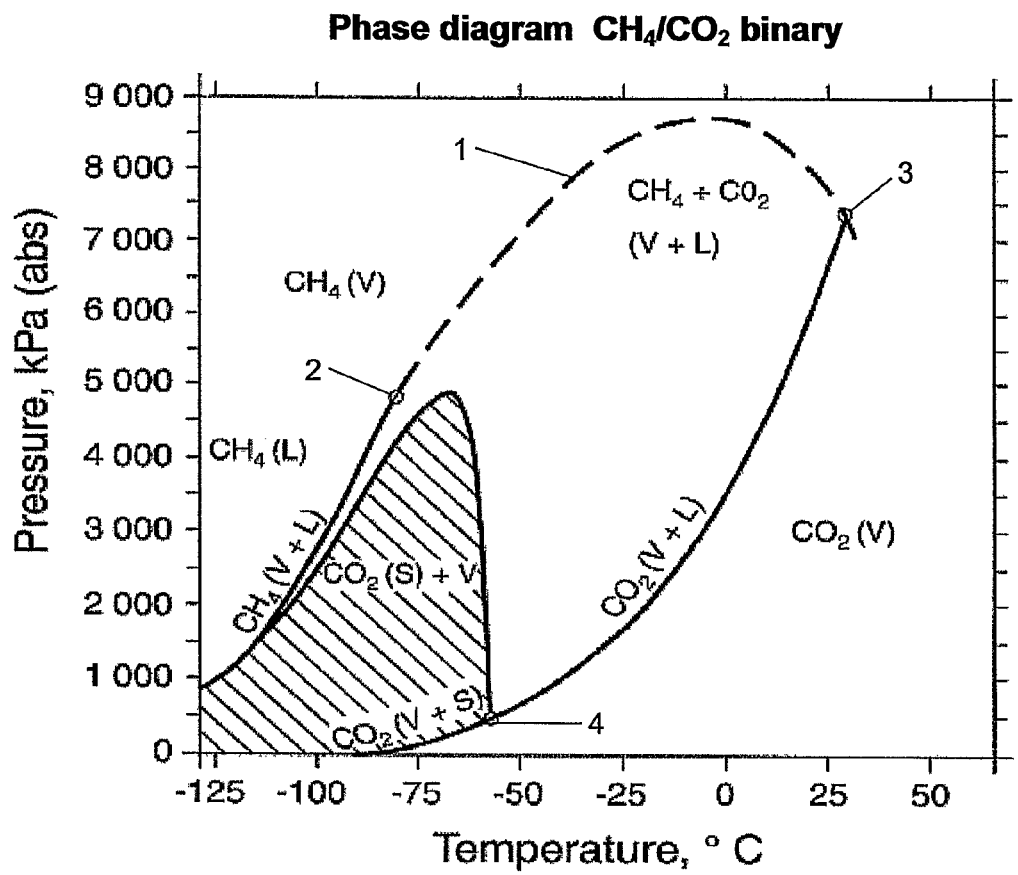

From FIG. 4, "Phase diagram $CH_4/CO_2$ binary", it follows that reducing the temperature below −65° C. will result in formation of solid $CO_2$.

Therefore, in a preferred embodiment, the final cooling will be attained using two parallel triple tube heat exchangers, wherein the first heat exchanger is cooling, while the other is defrosted, and visa versa. Using these alternating heat exchangers, a continuous gas flow may be created without interruption caused by freezing. It was found that it is very desirable to have two heat exchangers in parallel, because the problem of clogging as a result of processing solid/vapor/liquid $CH_4/CO_2$ mixtures, which problem is referred to often in the prior art (see e.g. GB-A-1 565 615 and U.S. Pat. No. 4,681,612 mentioned hereinabove) can be avoided in accordance with the present invention. Thus by using an apparatus having two heat exchangers, the present invention is able can be operated within the solid/vapor/liquid region since solidification, which may lead to e.g. clogging of the system, is allowed in one of the heat exchangers as the other exchanger is defrosting. Thus the apparatus which is proved in one embodiment of the invention allows for less rigid and less stringent process control, which is of course very desirable.

Since the temperature of liquefied $CO_2$ in the final cooling section is lower than the temperature of liquefied $CO_2$ from the first cooling section, also the partial pressure may differ. Therefore the liquefied $CO_2$ from the final cooling section may be heated to the same temperature as the first cooling section using a pre-cooler for the incoming biogas. Finally it can be controlled that both liquefied $CO_2$ streams from first and final cooling section are at the same temperature and pressure and will be stored in the liquefied $CO_2$ storage tank. A schematic diagram for stage 3 of the GPP is given in FIG. 2.

The efficiency of the system of the present invention is remarkably high. Loss of methane ($CH_4$) is less than 2% in comparison with techniques as pressure swing absorption and membrane technology which might result in about 15%-20% loss.

The advantages of the biogas treatment process that is the object of the present invention, noted following the performance of tests, may be summarized as follows.

Chilling the gas mixture to −25° C. will also lower the dew point of the gas to −25° C.;

If the gas mixture is heated after chilling, which is the normal procedure, condensation will no longer appear downstream the system;

The reduced activated carbon quantity saves both material and manpower/maintenance cost, as well cost related to the disposal of the activated carbon;

Downstream piping does not require heat tracing or insulation, providing additional cost benefits;

Another benefit is that some of lower boiling point contaminants (ammonia, hydrogen sulphide) and halides will be washed out of the gas as the moisture condenses; plus the solubility of these contaminants increases substantially at low temperatures;

Removing all contaminants including 2%-4% mol water will increase the caloric value of the gas by approximately 3% resulting in more electricity production per $Nm^3$ of gas;

Downstream (after step (a)) low-quality materials like SS304 or carbon steel can be used because condensation does not appear. This may also provide for a considerable cost benefit.

By way of example, the present invention will now described in further detail with reference to the non-limiting embodiments that are schematically represented in the accompanying FIG. 1 and FIG. 2.

Figure 2:
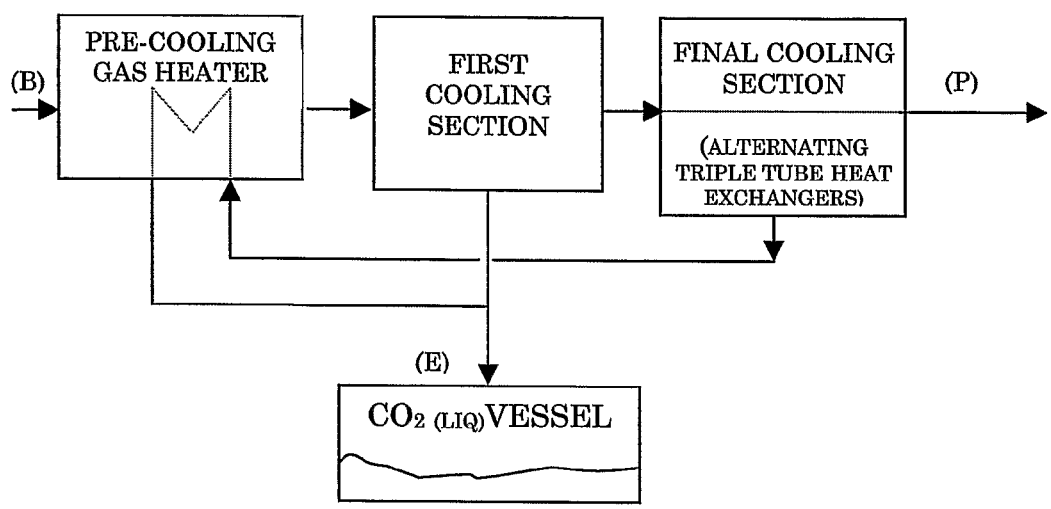

FIG. 1 is a diagram of the present invention. Referring to FIG. 1, biogas is produced by the bacterial degradation of waste in a landfill site or of another mass of organic waste. Typically 30%-50% of the gas produced is $CO_2$ and a small amount (no more than a few percent) is other impurity gases, especially $H_2S$, $SO_2$, halogens and siloxanes and the remainder is methane. Although the concentration of the other impurity gases is relatively small the impact to machinery is large. Hydrogen sulphide ($H_2S$) and halogens (F, Cl, Br, I) as well as halogen compositions tend to form acids which can corrode major components in the processing equipment. Also, traces of siloxanes, hydrogen sulphide, halogens and other minerals may reduce the performance and increase the maintenance of the gas engines that may be installed downstream the biogas production facility.

The biogas is drawn from the source and compressed to the required working pressure for $CO_2$ condensation. According to FIG. 3, required working pressure to achieve 90 mole % $CH_4$ at a minimum temperature of −80° C. is 1000 kPa.

Next the compressed biogas is fed to a gas/gas heat exchanger where the incoming gas is pre-cooled while the product gas (P), that will be re-heated well above its dew point. From the gas/gas heat exchanger the gas passes through a cold coalescer which removes the appeared moisture. Moisture residue is separated and drained at the separation point.

Next, the gas flows to a heat exchanger (e.g. a triple tube gas/gas heat exchanger), which chills gas mixture to approximately −25° C. Chilling gas condenses moisture, siloxanes and most other contaminants. Up to 99% of moisture may be captured in the first step. As the moisture freezes, it traps the contaminants, thereby reducing the chance for carryover in the outgoing treated gas. To achieve a continuous process two heat exchangers may be installed, which operate in an alternating sequence, viz. when one heat exchanger is in operation the second heat exchanger unit is switched off in order to defrost the frozen gas mixture containing the captured contaminants. The alternating sequence is repeated vice versa to provide continuous and uninterrupted gas flow. The heat produced in the heat exchanger that is in cooling mode, may be used to heat the heat exchanger that is in defrosting mode.

Treated gas is drawn through a re-polisher at a gas temperature of −25° C. The re-polisher is preferably an absorber filled with SOXSIA™ catalyst. Next purified gas is further deep-cooled in step (c) which is illustrated in FIG. 2.

Deep-cooling of the gas mixture is typically attained through three steps. By reducing the temperature of the gas mixture down to approximately 60° C. the dew point of $CO_2$ is achieved and condensation of $CO_2$ appears. In these conditions, approximately 50% of the $CO_2$ present can be liquefied.

Using the Wobbe Index of the outlet gas (P) composition, the final temperature of the gas may be controlled. At this final temperature the vapour/liquid equilibrium is such that it corresponds to the required Wobbe Index. This final temperature will vary between −65° C. and −80° C., depending on the required gas composition. From FIG. 3 it follows that the final temperature will decrease as the final mole fraction of $CH_4$ increases.

From FIG. 4 it follows that reducing the temperature below −65° C. will create solid formation of $CO_2$.

Therefore the final cooling will be achieved using two parallel triple tube heat exchangers where the first heat exchanger is cooling, while the other is defrosted visa versa. Using these alternating heat exchangers, a continuous gas flow is created without interruption caused by freezing.

Since temperature of the liquefied $CO_2$ in the final cooling section is lower than the liquefied $CO_2$ from the first cooling section, also the partial pressure differs. Therefore the liquefied $CO_2$ from the final cooling section will be heated to the same temperature as the first cooling section using a pre-cooler for the incoming biogas. Finally both liquefied $CO_2$ streams form first and final cooling section are at the same temperature and pressure and will be stored in the liquefied $CO_2$ storage tank.

In order to avoid hydrate formation of $CO_2$, $CH_4$, $H_2S$ and/or other hydrate forming species, the temperature limits are controlled and the pressure loss over both cooling steps (a) and (c) are preferably monitored. In case pressure loss increases to a certain preset maximum value the exchangers of the respective step switch position and hydrate/solid $H_2O$ (step (a)) or $CO_2$ (step (c)) can be removed in the defrosting mode.

Figure 3:
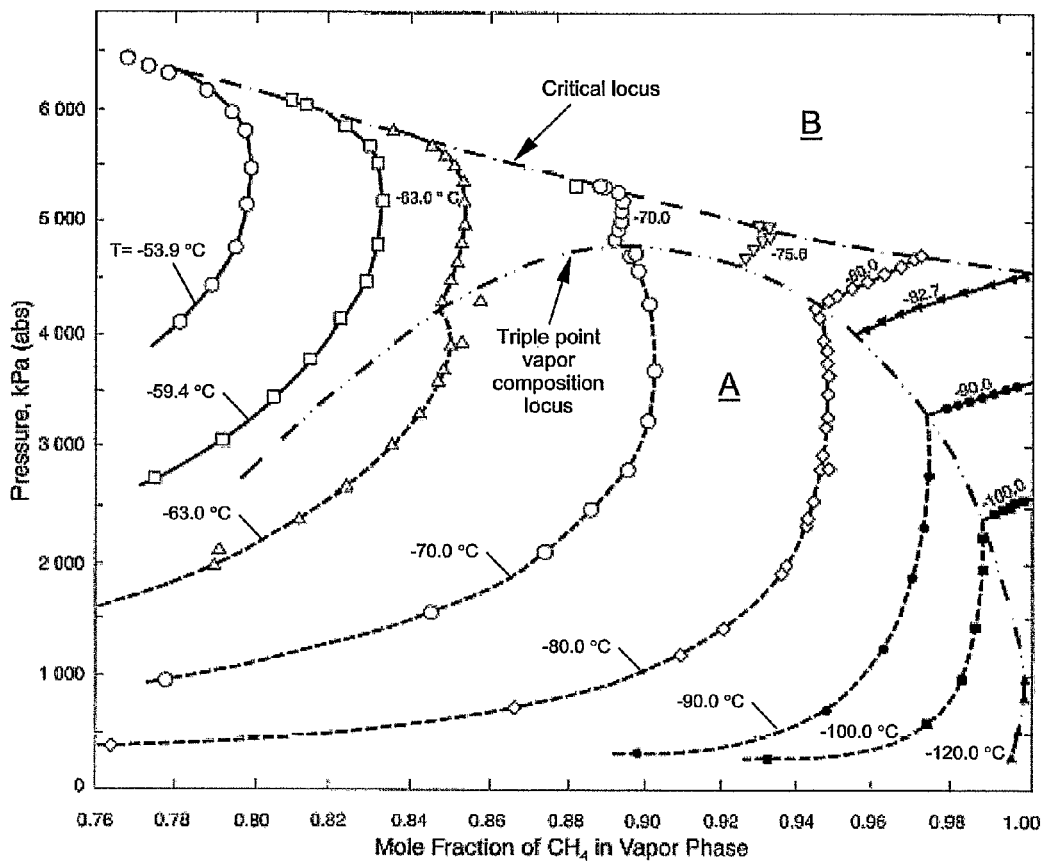
Figure 3:
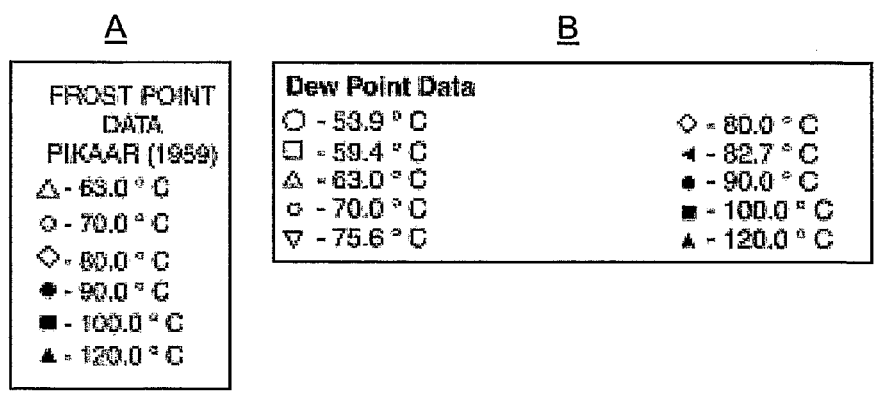

The driving force for achieving the required outlet composition is the (triple tube gas) heat exchanger in step (c) wherein liquid $CO_2$ from biogas is being evaporated in order to achieve the required $CO_2$ Vapour/Liquid equilibrium temperature (see FIG. 3). The equilibrium temperature and the feed conditions will determine the purity of the sellable gas. The equilibrium temperature control ensures fixed and stable Wobbe index of the sellable gas. The $CO_2$ used as refrigerant in this section can easily be recovered and subsequently offered to $CO_2$ users.

The invention claimed is:

1. Process for producing a purified methane comprising gas stream (P) from a methane containing gas stream (A), comprising the steps of:
   (a) pressurizing said methane containing gas stream (A) and subsequently cooling it, whereby a stream comprising condensed contaminants (C) and a methane comprising stream (B) are obtained, wherein said methane comprising stream (B) includes an amount of $CO_2$;
   (b) optionally feeding said methane comprising stream (B) to an adsorption unit or a catalytic conversion unit, whereby the concentration of contaminants in stream (B) is further decreased;
   (c) cooling the methane comprising stream (B) to a temperature, whereby condensated $CO_2$ is formed; and
   (d) removing said condensated $CO_2$ from said methane comprising stream (B),
   whereby said purified methane comprising gas stream (P) and a condensated $CO_2$ stream are obtained.

2. Process according to claim 1, wherein, in step (a), said methane containing gas stream (A) is cooled to a temperature of −25° C. or less.

3. Process according to claim 1, wherein said cooling in step (a) is carried out by feeding methane containing gas stream (A) to a first heat exchanger, while at the same time a second heat exchanger is allowed to defrost, optionally followed by switching said first heat exchanger and said second heat exchanger.

4. Process according to claim 3, wherein said first heat exchanger and said second heat exchanger are allowed to exchange heat between them.

5. Process according to claim 3, wherein said stream comprising condensed contaminants (C) is obtained from said second heat exchanger that is allowed to defrost.

6. Process according to claim 1, wherein said stream comprising condensed contaminants (C) comprises siloxanes.

7. Process according to claim 1, wherein said stream comprising condensed contaminants (C) comprises contaminants selected from the group consisting of water, $H_2S$, $SO_2$, halogen compounds, any hydrocarbon higher than methane and combinations thereof.

8. Process according to claim 1, wherein in step (c) said methane comprising stream (B) is cooled to a temperature of about −60° C.

9. Process according to claim 8, which is followed by a step, wherein said methane comprising stream (B) is cooled to a $CO_2$ vapour/liquid equilibrium temperature of −80° C. or less.

10. Process according to claim 1, wherein in step (b) said methane comprising stream (B) is fed to an adsorption unit and a catalytic conversion unit.

11. Process according to claim 10, wherein said adsorption unit and said catalytic conversion unit comprise a single unit comprising a bed of solid particles.

12. Process according to claim 1, wherein said methane containing gas stream (A) is a biogas, preferably obtained from a landfill, a digester, a wastewater treatment facility, or a combination thereof.

13. Apparatus for producing a purified methane comprising gas stream (P) from a methane containing gas stream (A), comprising:
(a) a compressor for pressurizing said methane containing gas stream (A), wherein said methane containing gas stream (A) includes an amount of $CO_2$; and a cooler unit located downstream of said compressor;
(b) optionally an adsorption unit or a catalyst conversion unit located downstream from said compressor and said cooler unit; and
(c) a second cooler unit connected to said adsorption unit or said catalyst conversion unit by piping for cooling said methane containing gas stream (A) to form condensated $CO_2$, said second cooler unit comprising an outlet for condensated $CO_2$, wherein said condensated $CO_2$ is equal to at least about half the amount of $CO_2$, and an outlet for said purified gas stream (P), wherein said second cooler unit comprises a first heat exchanger, and a second heat exchanger, which may be operated in parallel.

14. Apparatus according to claim 13, wherein said cooler unit under (a) comprises a first heat exchanger, and a second heat exchanger, which may be operated in parallel.

15. Apparatus according to claim 13, wherein the piping downstream of part (b) does not have any heat tracing or insulation.

16. Apparatus according to claim 13, wherein the said second cooler unit and said adsorption unit or said catalyst conversion unit downstream of part (a) are constructed from SS304, carbon steel, or combinations thereof.

17. Process according to claim 1, wherein said stream comprising condensed contaminants (C) comprises contaminants selected from the group consisting of water, $H_2S$, $SO_2$, halogen compounds, C5 and higher hydrocarbons, and combinations thereof.

* * * * *

UNITED STATES PATENT AND TRADEMARK OFFICE
CERTIFICATE OF CORRECTION

| | | Page 1 of 1 |
|---|---|---|
| PATENT NO. | : 8,673,056 B2 | |
| APPLICATION NO. | : 12/063916 | |
| DATED | : March 18, 2014 | |
| INVENTOR(S) | : De Bas et al. | |

It is certified that error appears in the above-identified patent and that said Letters Patent is hereby corrected as shown below:

IN THE SPECIFICATION:

Column 5, line 54:

Now reads: "$3_2O$"
Should read: -- 3 H2O --

Signed and Sealed this
Fifteenth Day of July, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,673,056 B2  
APPLICATION NO. : 12/063916  
DATED : March 18, 2014  
INVENTOR(S) : De Bas et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 132 days.

Signed and Sealed this

Twenty-ninth Day of September, 2015

Michelle K. Lee
*Director of the United States Patent and Trademark Office*